United States Patent [19]

Austin

[11] Patent Number: Plant 7,557

[45] Date of Patent: Jun. 18, 1991

[54] ROSE PLANT—AUSLEAF

[75] Inventor: David C. H. Austin, Albrighton, England

[73] Assignee: David Austin Roses, Albrighton, England

[21] Appl. No.: 435,556

[22] Filed: Nov. 9, 1989

[51] Int. Cl.[5] ..... A01H 5/00

[52] U.S. Cl. ..... Plt./1

[58] Field of Search ..... Plt./1

*Primary Examiner*—James R. Feyrer

*Attorney, Agent, or Firm*—Ladas & Parry

[57] ABSTRACT

A new variety of rose plant of the shrub class; distinctive in its character by its fully double flowers of yellow and pale orange/red, with abundant and continual blooming and the unusual blend of coloring and shaping of the flower.

1 Drawing Sheet

BACKGROUND OF THE INVENTION

The present invention relates to a new and distinct variety of shrub rose, seedling resulting from a definite effort to produce an improvement in this class of rose.

BRIEF SUMMARY OF THE INVENTION

Primary features of this new variety which connote a distinctive advance over existing types are the gross abundant and continual blooming that occurs for 5 months, taken with the perfection of the fully double flowers of an old-fashioned shape, more particularly apparent in the accompanying illustration of a specimen thereof. It is also noted that the unusual and pleasing petal coloration intensifies in color darkness with blossom age and exposure.

BRIEF DESCRIPTION OF THE DRAWING

The drawing is a color photographic representation of a new variety of flush of bloom taken substantially in side view and showing inflorescence in various stages, stems and foliage of the plant.

DETAILED BOTANICAL DESCRIPTION

The following is a detailed description of the new variety, colour terminology being in accordance with the "Methuen Handbook of Colour" published by Eyre Methuen Ltd (1963).

Variety denomination (in accordance with the UPOV Convention): Ausleaf (Trade name English Elegance).

Type: Hardy; bush; outdoor; seedling; for cut flowers and garden decoration.

Class: Shrub.

Propagation: Holds its distinguishing characteristics through succeeding propagations by budding.

The rose plant was grown at Albrighton, Nr. Wolverhampton, England and was derived as follows:

unknown seedling (applicant specification T/2/77)×unknown seedling (applicant specification A/32/76)

The operation of the artificial pollination is therefore expressed by the following (unknown seedling×unknown seedling).

The following observations are made of specimens grown outdoors in England.

PLANT DESCRIPTION

Plant:

*Height.*—140 cm.

*Habit.*—Tall, strong, upright.

Branches:

*Young stems.*—Colour: 29D6 Greyish green with faint reddish/pink 11A5 tinge. Texture: Glabrous, smooth. Thorns: 1-3 per node. 11D7 brownish voilet, 1B5 greyish yellow at apex.

*Old stems.*—Colour: 1E7 Moss green. Texture: Very smooth. Thorns: None.

Leaves:

*Stipules.*—Length: 15-21 mm. Width: 5-7 mm. Angle of wingtips to petiole: variable. Most often 45° or less. Colour: 1B5 greyish yellow. Margins: lined with pinky-red 11A6 glandular hairs. Shape: Wide and somewhat clasping at base, narrowing towards wing tips.

Petiole:

*General description.*—Sturdy.

*Length.*—65-88 mm (mature).

*Upperside color.*—27D7 Greyish green.

*Groove/hairs/thorns.*—Medium-sparse red 10B7 tipped glandular hairs.

*Underside.*—1B4 greyish yellow.

*Hair/thorns.*—Thorns 1A4 pastel yellow with reddish brown 8E8 tips. 1-2 per node. Sparse red 10A8 tipped glandular hairs tinge.

*Leaflets.*—Number: 5 and occasionally 7. Shape: Oval with cuspidate apex. Serration: Dentate. Texture: Leathery-tough.

General effect of foliage: Tall, semi-dense, semi-glossy.

Colour:

*Young foliage.*—Upperside: 29E7 Broken green. Voilet brown 11F8 shading especially on mid rib and margin. Underside: 29D6 greyish green with voilet brown 11F8 capillaries especially towards margins.

*Adult foliage.*—Upperside: 28F8 dark green. Underside: 29E5 greyish green.

INFLORESCENCE

Number of flowers per stem: most often 5.

Peduncle:

*Length.*—40–50 mm.

*Colour.*—1C6 greyish green with faint pinky/red tint 11A6.

*Thorns/hairs.*—Med. dense red 10B8 tipped glandular hairs.

Sepals:

*Upperside colour.*—29D7 greyish green. Pink red blush 11A4 midline and base red-tipped 10B8 apex.

*Outer margins.*—With red 10B7 tipped glandular hairs.

*Inner margins.*—Tomentose.

*Underside color.*—29D6 greyish green.

*Outside texture.*—Leathery, somewhat puckered. Red 10C8 tipped glandular hairs.

*Inside texture.*—Smooth. Densely tometose.

*Sepal length.*—20–25 mm.

*Bud shape.*—Ovoid with elongated cuspidate apex and flattened base.

*Length.*—25–30 mm.

*Max. width.*—Av. 10 mm.

*Colour when opening.*—29A5 viridine green at base turning to 2A3 pale yellow and 2A4 pastel yellow with pink tinges 12A3.

*Flower shape.*—Flat base. Convex top.

*Diameter.*—70–90 mm.

*Flower colour when opening.*—Upperside: Outer petals: 3A4–3A6 yellow at base, 6A2 orange white at top. Inner petals: 3A6 yellow at base, 8A4/5 pastel red at top. Underside: Outer petals: 3A6 yellow at base, 2A2 yellowish white at centre, 9A2 pinkish white at top edge. Inner petals: 3A5 yellow at base, 7A5/6 pastel red/reddish orange 7AB top edge.

*Flower colour when blooming.*—Flower colour characteristically varies in gradual shadings and in ranges from outer to inner petals, from side to side of the petal surfaces and with age of the flower. Ranges of petal coloration are typified by the following list of extremes of ranges. Upperside: 3A5/6 yellow at base, 3A6 yellow at base. Most of petal: 6A3 pale orange, 9A3 pale red. Underside: 3A5 yellow at base, 3A45 yellow at base. Most of petal: 5A2 orange white, 7A2 pinkish white.

*Flower colouring when finished blooming.*—Upperside: Outer petals: 2A4 Pastel yellow base, 7A2 pinkish white remainder. Inner petals: 2A4 pastel yellow base, 11A4 pastel pink remainder. Underside: Outer petals: 3A3 pale yellow base, 6A2 orange white remainder. Inner petals: 2A3 pale yellow base, 10A3 pale red remainder.

*Length of blooming season in location of production*.—End of June to beginning of October.

Fragrance: Good sweet musk type.

Lasting quality: Good. Lasting for 10–14 days on the plant and 12–14 days as cut flowers.

Petals:

*Shape outside.*—Roughly oval with flattened bi or tri-lobed top. Inside: Elongated ovoid with retuse apex.

*Texture.*—Slightly grainy.

*Number.*—40–50 inner±5 exhibit staminody.

*Cleaning.*—Medium.

Stamens:

*Number.*—About 70.

*Anthers.*—Golden yellow 4A8 maturing to dark brown.

*Filaments.*—Bright yellow 3A8.

Pistils:

*Number.*—About 70.

*Stigmas.*—Golden yellow 4A8.

*Styles.*—Greenish, 30A5 twisted.

Receptable:

*Colour.*—29D7 greyish green.

*Texture.*—Sparsley tomentose. Slightly rough.

*Size.*—10 mm×10 mm.

*Shape.*—Goblet shaped.

The development: Vegetation: vigorous.

Blooming: Abundant and continual for 5 months.

Aptitude to bear fruits: None.

Resistance to frost: Good.

Resistance to diseases: Very good.

I claim:

1. A new and distinct variety of rose plant of the shrub class, characterized as to novelty by its fully double flowers of yellow and pale orange/red, with abundant and continual blooming and the unusual blend of colouring and shaping of the flower being substantially as shown and described.

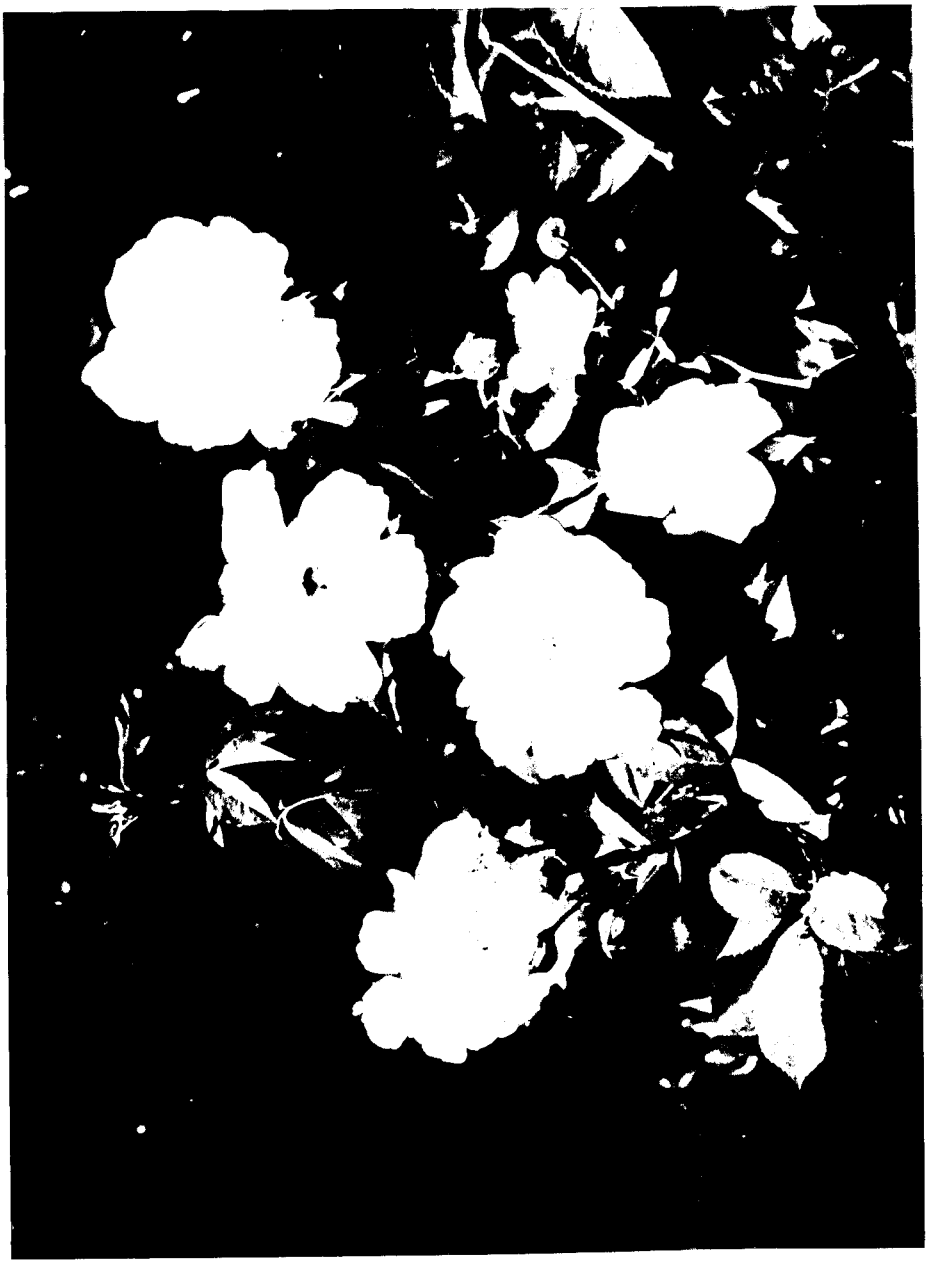

* * * * *